United States Patent [19]

Desmarais

[11] Patent Number: 5,024,701
[45] Date of Patent: Jun. 18, 1991

[54] DENTURE ADHESIVE COMPOSITION

[75] Inventor: Armand J. Desmarais, Wilmington, Del.

[73] Assignee: Hercules Incorporated, Wilmington, Del.

[21] Appl. No.: 291,412

[22] Filed: Dec. 22, 1988

Related U.S. Application Data

[63] Continuation of Ser. No. 671,277, Nov. 13, 1984, abandoned, which is a continuation-in-part of Ser. No. 519,331, Aug. 8, 1983, abandoned.

[51] Int. Cl.$^5$ .............................................. C09K 3/00
[52] U.S. Cl. ..................................... 106/35; 433/180; 523/120; 106/191
[58] Field of Search ........................ 433/180; 523/120; 106/35, 191

[56] References Cited

U.S. PATENT DOCUMENTS

| | | | |
|---|---|---|---|
| 2,978,812 | 4/1961 | Rosenthal | 32/2 |
| 2,997,399 | 8/1961 | Eberhard et al. | 106/35 |
| 3,440,065 | 4/1969 | LaVia | 106/35 |
| 4,280,936 | 7/1981 | Dhabhar et al. | 260/13 |

*Primary Examiner*—Amelia Burgess Yarbrough
*Attorney, Agent, or Firm*—Joanne L. Horn; Mark D. Kuller

[57] ABSTRACT

Disclosed are improved denture adhesive compositions containing a hydrophobically modified water-soluble polymer alone or admixed with an alkali metal salt of carboxymethyl cellulose having a D.S. of at least 0.3. Hydrophobically modified hydroxyalkyl celluloses and copolymers of ethylene oxide and long chain epoxyalkanes are preferred as the water-soluble polymer.

13 Claims, No Drawings

DENTURE ADHESIVE COMPOSITION

This is a continuation of application Ser. No. 06/671,277, filed Nov. 13, 1984, now abandoned, which is a continuation-in-part of the application, Ser. No. 519 331, filed Aug. 8, 1983, for Denture Adhesive Composition, now abandoned.

The use of dental prostheses as replacements for teeth is now widespread. Advances in the art, particularly in plastic and alloy chemistry, have made it possible to produce dentures which not only function better, but are markedly improved in appearance. The most common types of dental prostheses are (1) bridgework, fixed or removable, which are generally used to replace up to three missing teeth; (2) partial dentures, which are removable and are used when several teeth are missing; and (3) full dentures which are removable when all teeth of the upper or lower jaw or both have been removed or otherwise lost.

Concomitantly with the use of dentures, especially full dentures, denture adhesive compositions, first in powder form and later in cream form, were developed. Although there has been some dissent in the dental community as to whether denture adhesives should be used, they have come to be used extensively by the dental plate wearers. Basically, the dissenting opinion of the dental authorities rests on the belief that such adjuvant compositions are used as or become a substitute for proper fitting dentures or plates, and that the prior art denture adhesive compositions do not perform well under the wide range of conditions present in the oral cavity over any appreciable period of time, i.e., at least eight hours or more.

The denture adhesive is used by applying it to the face of the denture or plate which is particularly adapted to contact and mold itself to the contour of a particular oral surface in the mouth, and placing the denture in the mouth against and in contact with the oral surface.

Desirably, a denture adhesive should not be readily soluble in the fluids present in or taken into the mouth, should be resistant to the extreme changes in the temperature of the fluids taken in the mouth, and should be able to accommodate variations in the denture wearer's diet which results in diverse chemical characteristics, including pH. Further, the denture adhesive should have good adhesion or cohesion properties over a long period of time. These performance criteria are essential if the denture or plate is to be held in its place in the mouth by the denture adhesive composition, particularly during the mastication of foods and the drinking of beverages.

For years the majority of denture adherent powders or creams used to secure dentures in the mouth were prepared from finely ground particles of natural gums, such as karaya, acacia, guar, and tragacanth. The finely ground particles were dispersed in an anhydrous cream base, usually petrolatum, when the cream form was desired.

More recently, denture powders and creams have been prepared with cellulosic materials, such as sodium carboxymethyl cellulose, hydroxyethylcellulose, and hydroxypropylcellulose either alone or in combination with ethylene oxide homopolymers, acrylamide homopolymers and copolymers, or maleic anhydride derivatives to improve the adhesion properties of the denture powders and creams. Generally, such materials are dispersed in petrolatum, in a mineral oil, or in a mixture of petrolatum with a mineral oil as the carrier. Optionally, the mineral oil can be thickened with polyethylene.

These denture adhesive formulations provided some improvement over the traditional compositions containing only a natural gum in the powder form or a natural gum in a petrolatum carrier in the case of the cream form. However, these compositions only effectively secure the dentures in the mouth over short periods of time. Therefore, it has generally been necessary to apply more than one application of the denture adhesive per day in order to obtain and maintain sufficient adhesion throughout the day. Multiple applications of the adhesive are not only inconvenient, but are usually impractical if not impossible. Moreover, many of the commercially available denture adhesives have a greasy or oily mouthfeel. Hence, there is a need for a denture adhesive which exhibits superior adhesive properties over long periods of time, and which does not feel oily or greasy to the mouth tissues.

Moreover, it was and still is essential that the natural or synthetic polymer used in denture adhesive powders and creams be ground sufficiently fine to avoid a gritty mouthfeel. Generally, the particle size distribution is such that the polymeric material will pass through a 100 mesh to 200 mesh screen.

This invention provides denture adhesive compositions containing a hydrophobically modified water-soluble polymer alone or in combination with an alkali metal salt of carboxymethyl cellulose. The compositions of this invention afford superior adhesion or cohesion properties under the variable environmental conditions encountered in the mouth over a substantially increased period of time. Moreover, the compositions have a substantially reduced greasy or oily mouthfeel.

Additionally, the hydrophobically modified water-soluble polymers used in the denture adhesive compositions of this invention are not as hard a particulate matter as the conventional materials. Hence, they do not require as fine a grind as the conventional materials. For example, particles of the hydrophobically modified water-soluble polymers that pass through an 80 mesh screen, but are retained on a 100 mesh screen are suitable for this use.

The hydrophobically modified water-soluble polymers is generally present in an amount, by weight, of from about 5% to about 50%, preferably from about 5% to about 35%, and most preferably from 10% to about 35%.

Typically the hydrophobically modified water-soluble polymer is a hydrophobically modified cellulose ether or a copolymer of ethylene oxide and at least one long chain epoxyalkane.

Suitable hydrophobically modified cellulose ethers include water-soluble alkyl and hydroxyalkyl celluloses, such as methyl, hydroxyethyl, and hydroxypropyl cellulose which are further substituted with a hydrocarbon radical having from 8 to 25 carbon atoms, preferably from 12 to 20 carbon atoms, in an amount from about 0.2 weight percent to about the amount which renders the cellulose ether less than 1% by weight soluble in water. The cellulose ether to be modified is typically of low to medium molecular weight, i.e., less than about 800,000, preferably 20,000 to about 500,000. The preferred cellulose ether substrate is hydroxyethyl cellulose.

The term "'hydrocarbon radical" as used herein is meant to include the hydrocarbon portion as well as any other moiety present, such as an ester, ether or urethane moiety, as a result of the particular compound used to further substitute the cellulose ethers.

The hydrophobically modified cellulose ethers can be prepared by the method set forth in U.S. Pat. No. 4,228,277.

Suitable ethylene oxide copolymers include the copolymers of ethylene oxide with at least one 1,2-epoxyalkane containing from 8 to 25 carbon atoms, preferably from 12 to 20 carbon atoms. Desirably the copolymers contain, by weight, from about 96% to about 99.9% ethylene oxide and from about 4% to about 0.1% of the 1,2-epoxyalkane and have a molecular weight from about 20,000 to about 1,000,000.

The ethylene oxide copolymers can be prepared by the method set forth in U.S. Pat. No. 4,304,902.

The hydrophobically modified water-soluble polymer can be combined with a finely divided alkali metal salt of carboxymethyl cellulose, preferably the sodium or calcium salt. Preferably the salt of carboxymethyl cellulose has a degree of substitution (D.S.) of at least 0.3, a molecular weight of from about 50,000 to about 1,250,000, and is present in an amount, by weight, of from about 10% to about 45% when used in the cream form and from about 10% to about 95% when used in the dry form. Most preferably the D.S. is from about 0.6 to about 1.6 and the molecular weight is from about 300,000 to about 1,250,000. Degree of substitution is the number of carboxymethyl groups per anhydroglucose unit of the cellulose molecule.

The salt of carboxymethyl cellulose can be prepared by the method described in R. L. Whistler & J. N. BeMiller "Industrial Gums", 696 (2d ed. 1973).

The polymers used in the composition of this invention may be used directly as a denture adhesive in powder form. Alternatively, they can be mixed with an anhydrous cream carrier or vehicle to prepare a denture adhesive in cream form.

The carrier or vehicle can be petrolatum or petrolatum combined with mineral oil. The mineral oil can be admixed with a polyethylene. Generally, the carrier is present at a concentration of from about 35% to about 85% by weight. When a combination of petrolatum and mineral oil, or petrolatum and mineral oil containing a polyethylene, is used as the carrier, the petrolatum is present at a concentration of from about 40% to about 80% and the mineral oil or mineral oil containing a polyethylene at a concentration of from about 1% to about 15%.

In addition, the denture adhesive of this invention can contain other water swellable or soluble polymers, such as polyoxyethylene, polyacrylamide, acrylamide-acrylic acid copolymers, and maleic anhydride derivatives. Other excipient materials, such as fillers, flavoring agents, coloring agents and preservatives can also be included in the compositions of this invention. Typical fillers include dicalcium phosphate, calcium carbonate, and talc. The fillers can be present in an amount from about 0.1% to about 60% in dry denture adhesives, and from about 0.1% to 20% in cream denture adhesives.

To further illustrate this invention, various illustrative examples are set forth below.

All parts and percentages are by weight, unless otherwise specified, throughout the specification and claims.

EXAMPLE 1

This example illustrates an embodiment of the denture adhesive composition of this invention and how to prepare it.

Thirty-five (35)% hydrophobically modified hydroxyethyl cellulose having a molecular weight of 200,000 and having 0.7 by weight of $C_{16}$ alkane is added to 65% petrolatum in a mixing kettle and stirred until the ingredients are thoroughly mixed.

EXAMPLE 2

This example illustrates another embodiment of the denture adhesive composition of this invention.

The composition is prepared according to the procedure and formulation of Example 1 with the exception that a hydrophobically modified ethylene oxide polymer having a molecular weight of 50,000 and having 0.7% by weight of a 1,2-epoxyalkane is used instead of the modified hydroxyethyl cellulose of Example 1.

EXAMPLE 3

This example illustrates another embodiment of the denture adhesive composition of this invention.

The composition is prepared according to the procedure of Example 1 with the formulation of Example 1 except that 10% of the hydrophobically modified hydroxyethyl cellulose and 50% petrolatum is used, and 40% of the sodium salt of carboxymethyl cellulose (CMC) having a D.S. of 0.7 is added.

EXAMPLE 4

This example illustrates another embodiment of the denture adhesive composition of this invention.

The composition is prepared according to the procedure of Example 1 with the formulation of Example 3 except that 10% of the hydrophobically modified ethylene oxide polymer of Example 2 is used instead of the hydrophobically modified hydroxyethyl cellulose.

EXAMPLE 5

This example illustrates another embodiment of the denture adhesive composition of this invention.

The composition is prepared by dry blending 20% of the hydrophobically modified hydroxyethyl cellulose of Example 1, 50% CMC having a D.S. of 0.7, and 30% dicalcium phosphate.

EXAMPLE 6

This example illustrates another embodiment of the denture adhesive composition of this invention.

The composition is prepared according to the procedure of Example 5 with the formulation of Example 5 except that the hydrophobically modified ethylene oxide polymer of Example 2 is used instead of the hydrophobically modified hydroxyethyl cellulose.

To characterize the compositions of this invention the following tests were conducted.

Adhesion test: A 3"×¾" methylmethacrylate plate and a 3"×¾" spunbonded polyester sheet are dipped in distilled water. A 0.5 g. sample of the denture adhesive composition is placed on and spread over a 2" length of the plate. The plate is covered with the spunbonded polyester sheet, and then manually pressed flat.

The test plate is then placed in a crystallization dish filled halfway with distilled water and equipped with a magnetic stirrer. The dish is covered with aluminum foil and placed on a stirrer base which is set for light agitation. Stirring is maintained for 4 hours to age the samples.

After 4 hours, the test plates are removed from the dish and blotted dry with paper towels. The bond strength (adhesion) is then measured on an Instron tester, equipped with Microcon 2 data acquisition system, at a rate of pull of 5"/minute. The peak load is printed out in grams of force.

Tack and stiffness test: One gram (1.0 g.) SD Alcohol 40 is added to 10 g. of the denture adhesive composition in a 150 ml. beaker and stirred with an aluminum spatula until the ingredients are thoroughly mixed. Nineteen grams of distilled water (19.0 g.) are added and stirring is continued until a homogeneous mixture is obtained. The mixture is then transferred to a Petri dish and evenly distributed over the bottom of the Petri dish with the spatula. The dish is covered and allowed to set for 24 hours.

The dish is uncovered and centered on the sample plate of a Voland Stevens LFRA texture analyzer. A ½" diameter butyl methacrylate probe is activated at 1 mm/sec. and placed at a depth of 4 mm into the sample. The resistance and adhesion to the probe, which is a measurement of stiffness and tack, respectively, is recorded in grams.

The test results for the compositions of this invention embodied in Examples 1-6 are set forth in Table 1 below.

TABLE 1

| Example No. | Adhesion (g.) | Stiffness (g.) | Tack (g.) |
|---|---|---|---|
| 1 | 95 | 210 | 35 |
| 2 | 110 | 180 | 50 |
| 3 | 140 | 280 | 45 |
| 4 | 160 | 230 | 55 |
| 5 | 140 | 290 | 40 |
| 6 | 170 | 210 | 60 |

Thus, this invention provides a novel denture adhesive composition having superior adhesion characteristics.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. A denture adhesive composition consisting essentially of (a) from about 5% to about 50% of a hydrophobically modified water-soluble polymer selected from the group consisting of a hydrophobically modified cellulose ether wherein the cellulose ether is substituted with a hydrocarbon radical having 8 to 25 carbon atoms in an amount from about 0.2 weight percent to about the amount which renders the cellulose ether less than 1% by weight soluble in water and a copolymer of ethylene oxide and at least one long chain epoxyalkane having 8 to 25 carbon atoms; (b) from about 35% to about 85% of petrolatum; and (c) 0% to about 15% of a material selected from the group consisting of mineral oil and mineral oil admixed with a polyethylene.

2. The composition of claim 1 wherein the hydrophobically modified water-soluble polymer is a hydrophobically modified cellulose ether wherein the cellulose ether is selected from the group consisting of alkyl cellulose and hydroxyalkyl cellulose.

3. The composition of claim 2 wherein the hydrophobically modified cellulose ether is a hydroxyethyl cellulose substituted with a hydrocarbon radical having 8 to 25 carbon atoms in an amount from about 0.2 weight percent to about the amount which renders the hydroxyethyl cellulose less than 1% by weight soluble in water.

4. The composition of claim 1 wherein the copolymer is a copolymer of ethylene oxide and at least one 1,2-epoxyalkane having 8 to 25 carbon atoms.

5. The composition of claim 4 wherein the copolymer contains, by weight, from about 96% to about 99.9% ethylene oxide and from about 4% to about 0.1% of the 1,2-epoxyalkane.

6. A denture adhesive composition consisting essentially of (a) from about 5% to about 35% of a hydrophobically modified water-soluble polymer selected from the group consisting of a hydrophobically modified cellulose ether wherein the cellulose ether is substituted with a hydrocarbon radical having 8 to 25 carbon atoms in an amount from about 0.2 weight percent to about the amount which renders the cellulose ether less than 1% by weight soluble in water and a copolymer of ethylene oxide and at least one long chain epoxyalkane having 8 to 25 carbon atoms; (b) from about 10% to about 45% of an alkali metal salt of carboxymethyl cellulose; (c) from about 40% to about 80% of petrolatum and (d) 0% to about 10% of a mineral oil and a mineral oil admixed with a polyethylene.

7. The composition of claim 6 wherein the hydrophobically modified water-soluble polymer is a hydrophobically modified cellulose ether selected from the group consisting of alkyl cellulose and hydroxyalkyl cellulose.

8. The composition of claim 7 wherein the hydrophobically modified cellulose ether is a hydroxyethyl cellulose substituted with a hydrocarbon radical having 8 to 25 carbon atoms in an amount from about 0.2 weight percent to about the amount which renders the hydroxyethyl cellulose less than 1% by weight soluble in water.

9. The composition of claim 6 wherein the copolymer is a copolymer of ethylene oxide and at least one 1,2-epoxyalkane having 8 to 25 carbon atoms.

10. The composition of claim 9 wherein the copolymer contains, by weight, from about 96% to about 99.9% ethylene oxide and from about 4% to about 0.1% of the 1,2-epoxyalkane.

11. The composition of claim 6 wherein the alkali metal salt of carboxymethyl cellulose has a D.S. of at least 0.3.

12. The composition of claim 6 wherein the alkali metal salt of carboxymethyl cellulose has a D.S. of from about 0.6 to about 1.6.

13. The composition of claim 1 which further comprises from about 0.1% to about 60% of a filler.

* * * * *

UNITED STATES PATENT AND TRADEMARK OFFICE
CERTIFICATE OF CORRECTION

PATENT NO. : 5,024,701
DATED : June 18, 1991
INVENTOR(S) : Armand J. Desmarais It is certified that error appears in the above-identified patent and that said Letters Patent is hereby corrected as shown below:

Col. 4, line 8 "0.7" should read --0.7%--.

Signed and Sealed this

Twentieth Day of October, 1992

Attest:

DOUGLAS B. COMER

*Attesting Officer*  *Acting Commissioner of Patents and Trademarks*